United States Patent [19]

Sandham et al.

[11] Patent Number: 4,496,322

[45] Date of Patent: Jan. 29, 1985

[54] BENZOIN ANTIMICROBIAL DENTAL VARNISHES

[75] Inventors: H. James Sandham, Thorhill; Thomas E. Balanyk, Toronto, both of Canada

[73] Assignee: University of Toronto Innovations Foundation, Toronto, Canada

[21] Appl. No.: 493,755

[22] Filed: May 11, 1983

[51] Int. Cl.³ ............................................... A61K 6/08
[52] U.S. Cl. ..................................... 433/217; 106/35; 106/237
[58] Field of Search ............... 106/35, 237; 424/34, 424/181, 196, 326; 536/7.2; 433/217

[56] References Cited

U.S. PATENT DOCUMENTS 3,049,474  8/1962  Hepworth ........................... 424/34
3,689,673  9/1972  Phares ................................. 424/326
3,855,140 12/1974  Billany et al. ...................... 424/326

OTHER PUBLICATIONS

Reynolds et al., *Martindale, The Extra Pharmacopoeia*, 1982, pp. 314 and 1362.
*Japanese Journal of Bacteriology*, vol. 21, pp. 609–613.

*Primary Examiner*—Lorenzo B. Hayes
*Attorney, Agent, or Firm*—Lalos, Leeds, Keegan, Lett, Marsh, Bentzen & Kaye

[57] ABSTRACT

A composition for treating dental infections, e.g. dental caries caused by *Strep. mutans,* comprises a varnish containing an antimicrobial agent such as chlorhexidine acetate and benzoin gum in an orally acceptable liquid. The composition can be painted on teeth, allowed to dry thereon to give a transparent, translucent or tooth colored film which is effectively invisible but provides sustained release of the antimicrobial agent to the site of infection over a period of at least four days. The film can be removed at will, e.g. by application of the liquid varnish base.

5 Claims, 3 Drawing Figures

BENZOIN ANTIMICROBIAL DENTAL VARNISHES

FIELD OF THE INVENTION

The present invention relates to compositions and methods for treatment and prevention of oral infections.

BACKGROUND

Evidence is accumulating which indicates that both dental caries and periodontal disease may result from infection by specific components of the oral microflora. Elimination of these infections should therefore contribute to treatment and prevention of these disorders.

It is known to apply antiseptics topically to teeth, gums etc. as mouthwashes and in gels. Systemic administration of antibiotics is sometimes prescribed for treatment of periodontal disease. While both such methods are effective in reducing oral bacterial counts, the active ingredients seldom remain at the site of infection in effective concentration for a time long enough for fully effective treatment. Topically applied liquid antiseptics such as mouthwashes are easily washed from the infection site by salivation and routine mastication.

A properly effective, convenient and patient-acceptable means for effecting treatment of dental infections, such as dental caries caused by *Strep. mutans* infections, has not heretofore been developed. Such a means needs to be effective to contact the site of infection with the antimicrobial treating agent over an extended period of time, for example several days. Moreover, it should be capable of effecting treatment without the over-frequent or continuous adjustments, modifications, inspections and monitorings requiring professional attention. It must of course resist premature removal from the infected site as a result of normal salivation, mastication and intake of food and beverage. Finally, but equally importantly, it must be acceptable to the patient, in terms of its taste, external appearance, texture, effect on oral sensitivities, odour, and freedom from interference with normal oral functions.

BRIEF REFERENCE TO THE PRIOR ART

It is also known to use a composition consisting of compound benzoin tincture binder, benzocaine and cetylpyridium chloride with other ingredients, for oral topical application for treatment of canker sores (Blistex Incorporated, "Kank-A"). Such a composition is not, however, suitable for application to teeth to treat or prevent dental caries. Firstly, the formulation contains ingredients which impart an unpleasant, bitter taste thereto, so that it is not acceptable for use in applications where it will be retained in the oral cavity for extended periods of time. Secondly, it imparts discoloration to teeth when applied thereto. Thirdly, it contains toxic ingredients.

SUMMARY OF THE INVENTION

It is an object of the present invention to provide an oral composition effective for combatting growth of infection causing bacteria and capable of adherence to the infection site, and retention in the oral cavity.

It is a further object of the present invention to provide a novel, orally acceptable composition which has acceptable taste and color characteristics to permit its use on patients' teeth for periods of time necessary to effect treatment of dental caries infection.

It is a further object of the invention to provide a method of combatting and treating oral infections.

In one aspect of the present invention, a composition suitable for dental use and effective in combatting growth of disease causing bacteria is provided, the composition comprising at least one antimicrobial agent, and a dentally and biologically acceptable binder material. The composition as a whole can be adhered to the site of dental infection. The binder material is capable of permitting effective communication of said antimicrobial agent with the infection site when the composition is applied thereto, over an extended period of time, to effect treatment. The residue of the composition after treatment is readily removed at will.

DESCRIPTION OF THE PREFERRED EMBODIMENTS

Figure 1:
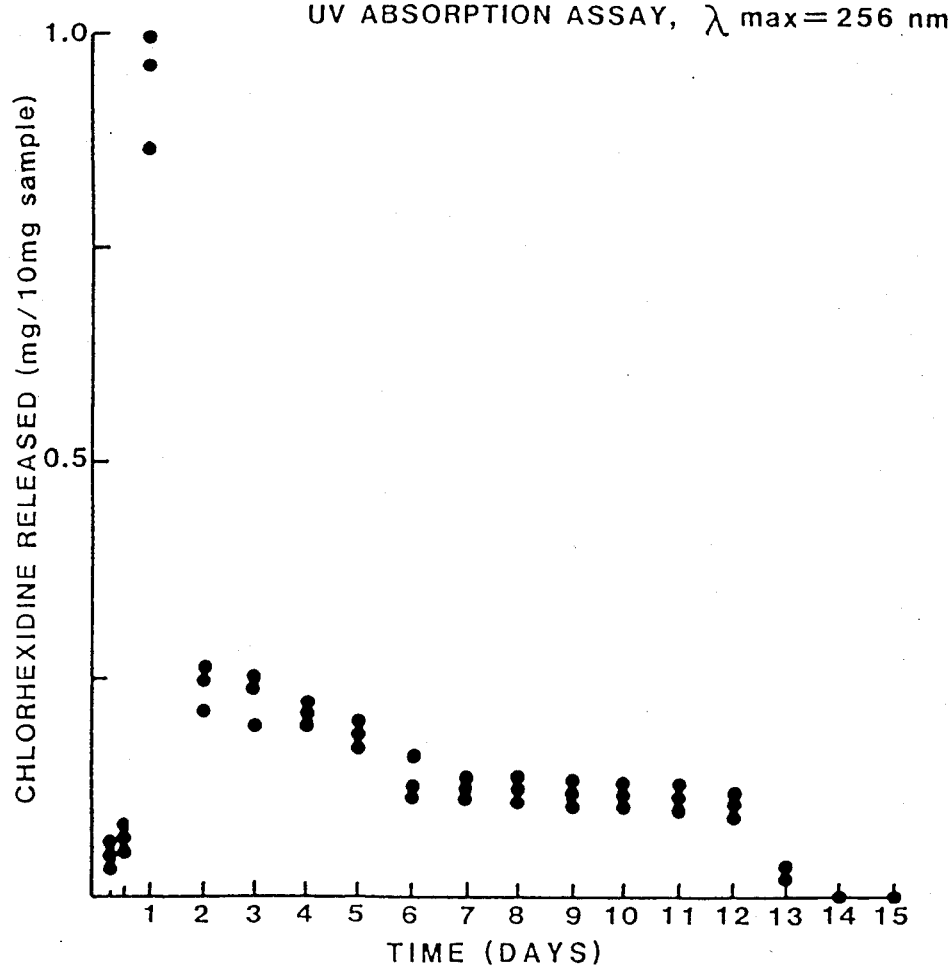

The composition may initially be prepared in any form suitable for application to teeth and/or gingiva, in the oral cavity, such as pastes, liquids, semi-solids or the like, provided that the binder and antimicrobial agent adhere to the structures to which they are applied. Suitably, the composition is initially prepared in the form of a liquid varnish, in an appropriate solvent, and applied to oral structures as such. After application, the solvent evaporates to leave a solid deposit, film or coating on the structure to which it has been applied. The solid consists essentially of the binder material and the antimicrobial agent or agents. The binder material permits a slow release of the antimicrobial agent or agents to the applied site, for prolonged treatment of the site therewith.

A specific preferred binder material is benzoin gum, either Sumatra or Siam benzoin, or fractions or recombined fraction thereof (hereinafter referred to as benzoin for brevity), which is capable of adherence to the tissues and enamel of the gingiva and teeth respectively. The benzoin is soluble in ethanol, which constitutes a suitable solvent to make the varnish composition, and is also compatible with several suitable antimicrobial drugs. After application to the infected site, a composition formed from the benzoin, ethanol and antimicrobial agent dries to form a solid, permitting a sustained release of the active antimicrobial ingredient over an extended period of time. Repeated applications for compositions of the present invention are not required on a frequent basis, for effective treatment. It has been found that the antimicrobial agent is effectively maintained at the infection site for at least four days owing to the presence of the benzoin film. The composition can be removed at will, by application of the appropriate solvent, normally ethanol, to the solid or by other standard oral hygiene techniques.

Preferred compositions according to the present invention include a plurality of antimicrobial agents.

A wide variety of antimicrobial agents can be used in compositions according to the invention, choice among which is determined largely on the basis of the infection which it is required to combat and safety to the patient. Erythromycin and chlorhexidine are examples of suitable preferred agents for combatting common oral bacterial infections.

Chlorhexidine is preferably used in the form of an orally acceptable salt thereof, e.g. acetate, hydrochloride or gluconate. Most preferred among chlorhexidine salts in chlorhexidine acetate on account of its appropriate solubility in water and in the preferred solvent ethanol, to provide good rate of release from the film.

The relative proportions of binder, antimicrobial agents and solvent in the preferred composition can vary widely. The lower solvent limit is fixed only by the maximum solubility of the other ingredients therein. The ratio of antimicrobial agent to solvent can be anywhere from 0.001% w/v up to a saturated solution thereof, e.g. 20%. The ratio of antimicrobial agent to binder is suitably in the range 10:1 to 1:10 by weight, preferably 5:1 to 1:5, and most preferably 2:1 to 1:2. Precise preferred ratio depends to some extent on the rate of release of the antimicrobial agent from the film. It is preferred to subject the site of infection initially to relatively large amounts of antimicrobial agent, to reduce the chance of formation of antimicrobial resistance in the infection.

Compositions according to the present invention are best formulated from only three essential ingredients, namely the benzoin binder, the ethanol solvent, and the antimicrobial agent or agents. Such a composition contains only orally acceptable, nontoxic ingredients. It contains no ingredients likely to have the effect of discoloring the dental site to which it is applied. With choice of the most appropriate antimicrobial agents, the hardened film contains no ingredients imparting thereto an unacceptable taste or texture, rendering it unpleasant to the user. It is suitably and conveniently applied by painting onto the site of infection. It adheres strongly to the teeth or gums, and penetrates effectively into all fissures and pits on the tooth surface. After application to the teeth, the composition dries in a relatively short period, e.g. about 3–6 minutes to yield a strongly adherent, clear or tooth-colored film which is effectively invisible whilst in place. It is strong enough to remain on the teeth for an extended period of time, at least four days, and will resist the forces commonly applied during mastication. Whilst the film is in place, of course, the user must refrain from application thereto, of the solvent ethanol as part of the user's drink intake, but the film can nevertheless be removed as and when required, at will, by simple application thereto of ethanol solvent an employment of standard oral hygiene procedures. Whilst in place, the film releases the antimicrobial agent or agents contained therein at a slow, relatively constant rate, and in concentration sufficient effectively to combat the target bacteria over a period of several days. Finally, the solvent used, namely ethanol, is compatible with restorations present in the teeth as well as original tooth enamel and does not dissolve or soften them. If desired, the composition may additionally include small amounts of additional ingredients such as flavorants or flavor maskers texturizers or other tooth treating aids such as fluorides.

In addition to application to teeth, gingiva etc. by painting thereon as a liquid, dryable varnish, one can also apply compositions of the invention as pastes, e.g. in a toothpaste formulation, as a liquid mouthwash, as a chewable tablet or the like, as long as an adherent film of binder and antimicrobial agent is applied in a semi-permanent manner to the site of infection, e.g., at least overnight.

BRIEF REFERENCE TO THE DRAWINGS

Figure 2:
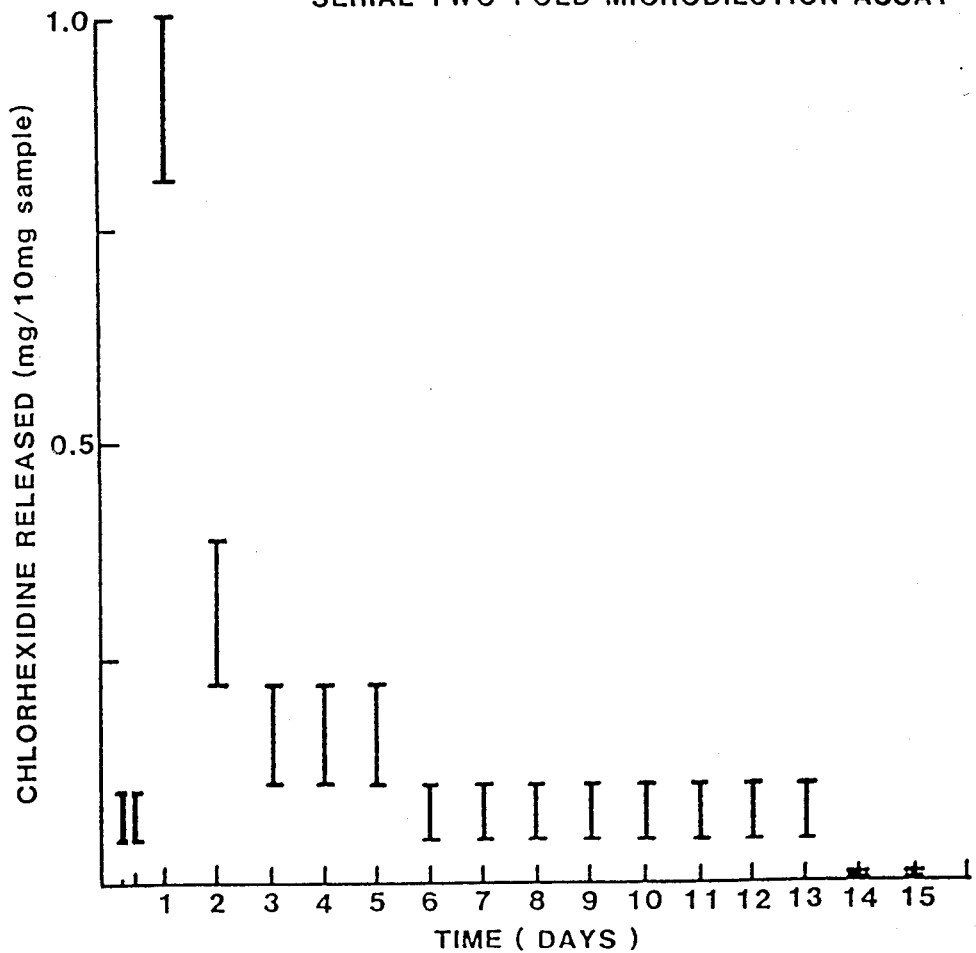
Figure 3:
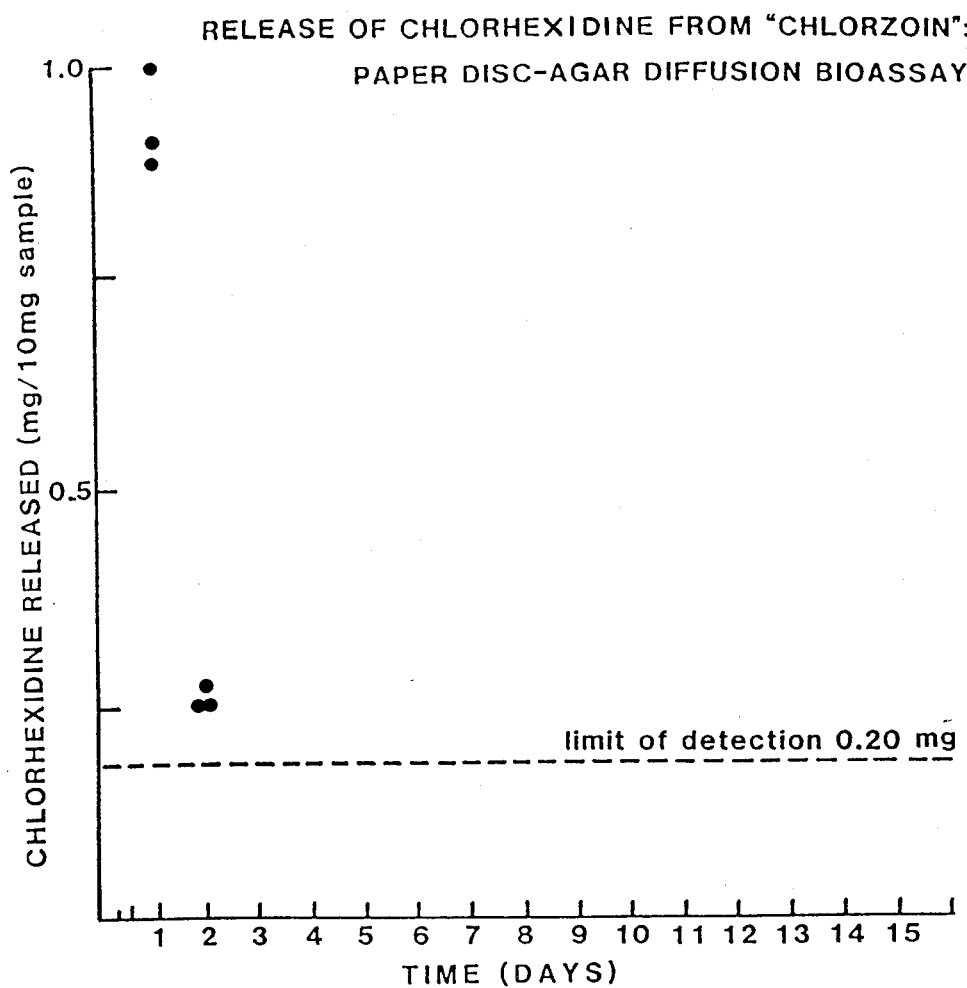

FIGS. 1, 2 and 3 are graphical representation of the results of experiments reported in Example 4.

The invention is further described in the following specific, nonlimiting examples:

EXAMPLE 1

Varnish Formulation

A formulation according to the invention was made by dissolving 1 gm chlorohexidine acetate in 10 ml of tincture of benzoin, which consisted of a 10% w/v solution of Sumatra benzoin in 95% ethanol, (hereinafter referred to as "CHLORZOIN"* formulation). A similar formulation was prepared using erythromycin in place of chlorhexidine (to form an "ERYTHROZOIN"* formulation). These liquid formulations were then used as varnishes, to paint and coat oral structures for a temporary period, as described in the subsequent examples.

EXAMPLE 2

Extracted molars, with clear fissures and containing neither visible caries nor amalgams, were provided. The apical foramen of each tooth was sealed with methyl-2-cyanoacrylate and then the teeth were dried for 24 hours at 22° C. The teeth were then placed in 95% ethanol for 24 hours and dried for four hours at 37° C. in covered sterile petri dishes.

Each molar was placed in a tube containing a 20 ml solution of Todd Hewitt broth (THB) and 5% sucrose. Nine tubes were inoculated with 0.1 ml of JC2 strain of S. mutans ($10^8$/ml in tryptic soy) and another nine molar-containing tubes were inoculated with a 0.1 ml of a mixture of S. mutans (comprised of E-49, BHT, JC2, PS-14, PS-72, 01H1, 6715, PK1, LM7 and ATCC 10499) of varying concentrations.

The molar and broth-containing tubes were incubated for 72 hours in a 90% $N_2$, 10% $CO_2$ atmosphere in standard incubating jars at 37° C. whereafter the teeth were removed and aseptically transferred to covered sterile petri dishes where they were dried for 2 hours in a warm room (37°).

Nine teeth grown in broth containing only the JC2 strain were painted with 0.1 ml of different varnishes prepared according to Example 1. The first group of three was painted with tincture of benzoin. The second group was painted with CHLORZOIN. ERYTHROZOIN was painted on the teeth forming group three.

A similar test was performed on nine teeth incubated with the multi-strain inoculated tubes.

The painting was performed with Fluor-Protector disposable brushes manufactured by Ivoclar-Vivadent. The brushes were gas sterilized before use.

After application of the varnish, the coated teeth were dried on covered sterile petrie dishes for 30 minutes at 37° C.

All teeth were then placed in 100 ml THB (5% sucrose) solution for 24 hours at 37° C. under 90% $N_2$ and 10% $CO_2$ atmosphere.

The varnishes were then removed with rotating bristle brushes in a slow speed dental handpiece.

To analyze bacterial growth, each tooth was placed in 100 ml of Shklair's medium) at 37° C. for 14 days (90% $N_2$ and 10% $CO_2$ added). The results are shown in Table I. Bacterial growth is indicated by a change of medium colour from purple to yellow, indicated by "+" in the table below which summarized the results of the procedure supra.

TABLE I

| Varnish + JC2 | | | | Varnish + mixture | | | |
|---|---|---|---|---|---|---|---|
| Tooth | Benzoin | CZ | EZ | Tooth | BZ | CZ | EZ |
| 1 | + | | | 10 | + | | |
| 2 | + | | | 11 | + | | |
| 3 | + | | | 12 | + | | |
| 4 | | − | | 13 | | − | |
| 5 | | − | | 14 | | − | |
| 6 | | − | | 15 | | − | |
| 7 | | | − | 16 | | | − |
| 8 | | | − | 17 | | | − |
| 9 | | | − | 18 | | | − |

"+" indicates a color change, and
"−" indicates no color change, after fourteen days Table 1 indicates the efficacy of the CHLORZOIN and ERYTHROZOIN varnishes in inhibiting growth of *S. mutans* strains in vitro.

EXAMPLE 3

In vivo testing of tincture of benzoin and of CHLORZOIN.

An in vivo trial was undertaken using tincture of benzoin, both with and without chlorhexidine, as described in Example I in the mouth of one of the investigators. The handling and other properties of the preparations were found to be as satisfactory as in vitro properties. The film formed on the teeth in vivo closely resembled that formed in vitro. Additionally, the taste of the tincture of benzoin, although balsamic, was not objectionable to the patient. However, when CHLORZOIN was applied, its taste was objectionable. The taste became acceptable, however, when the teeth were first isolated from one another and dried using cotton roll prior to application of the CHLORZOIN. The cotton rolls were left in place until after the CHLORZOIN had hardened (a few minutes).

EXAMPLE 4

Kinetics of Release of Chlorhexidine From Films of "Chlorzoin"

The purpose of using varnish as a vehicle for delivering chlorhexidine was to release low levels of chlorhexidine slowly over a period of days in the vicinity of the tooth surface, the only site of *S. mutans* colonization in the mouth.

As an aid for predicting the rate of release of chlorhexidine from CHLORZOIN in the oral cavity, in vitro experiments in which solidified films of CHLORZOIN, of standardized weight (10 mg chlorhexidine and 10 mg of benzoin) and shape, were utilized. The lens-shaped films were prepared by pipetting 0.1 ml of CHLORZOIN into standardized moulds, and permitting them to dry in the air. The films were then placed in 10 ml of TRIS buffer for 15 days. The buffer solutions were constantly agitated and were completely replaced after 6, 12, and 24 hours and daily thereafter.

The removed buffer solutions were then assessed for their chlorhexidine content by three methods that were, in preliminary experiments, found to provide reproducible assessments of chlorhexidine concentration. The methods were (i) UV absorption at 256 μm, (ii) seial two-fold microdilution (Little et al., 1979), and (iii) paper disc-agar diffusion (Barry, 1981). The last two methods are biological assays, utilising antimicrobial effectiveness to estimate chlorhexidine concentration.

The results are presented graphically in appended FIGS. 1, 2 and 3, derived from triplicate test samples. They show chlorhexidine release for each time interval from 0.02 g of dried CHLORZOIN film. Following a slow initial release of chlorhexidine for the first 12 hours, there was an almost 10-fold greater release during the second 12 hour period. However, by the end of the third day, chlorhexidine release had decreased to approximately 0.1 mg per sample per day. Thereafter, it maintained an almost constant rate of release until approximately the 11th day, when the release rate began to fall off to zero by 14 days.

From these results it may be concluded that CHLORZOIN is capable of releasing chlorhexidine at a low rate over a period of several days, consistent with its use for eliminating *S. mutans* from the human oral cavity. The concentration of chlorhexidine attained in each sample of buffer solution during the period of slow release (approximately days 3 to 11) was approximately 10 μg/ml, a concentration which is known to be bactericidal in vitro for *S. mutans*. Thus, the concentration of chlorhexidine released during the slow release period seems potentially adequate to kill *S. mutans* in the immediate vicinity of the teeth.

The above data can also be used to provide a rough estimate of the maximum dose to a patient over a 24 hour period. The amount of CHLORZOIN required to coat the teeth of an adult subject with a complete natural dentition was found to be approximately 1.5 ml, approximately 15 times greater than that in each sample in these in vitro experiments. The results reported here (FIGS. 1, 2 and 3) indicate that approximately 1.2 mg of chlorhexidine was released in vitro over the first 24 hours, the period of maximum release. If the release rate were assumed to be similar in the human mouth, a human might be expected to ingest a maximum of approximately 18 mg of chlorhexidine (1.2 mg × 15) over a 24 hour period. This amount is well below that generally recognized as safe in humans.

An important feature of the present invention is that the compositions, when applied to teeth, are not readily visible to the outside observer. The films are colorless, clear or translucent, or the same essential color as the teeth themselves. They thus are acceptable both to the dental profession and the user, as an unobtrusive and convenient aid to dental care, which will not risk causing discoloration of the teeth afterwards. Moreover, they are easily formulated so as to be quite acceptable as to taste.

While the invention has been illustrated with reference to certain specific working examples, its scope is not to be construed as limited thereby. The scope of the invention is limited only by the scope of the appended claims.

We claim:

1. A dental varnish composition suitable for painting onto teeth to combat oral infection, said composition consisting essentially of:
   an orally acceptable liquid vehicle;
   benzoin;
   and at least one dentally acceptable antimicrobial agent selected from the group consisting of erythromycin, chlorhexidine and salts thereof and compatible with the liquid vehicle and the benzoin;
   said composition being capable of drying to form a solid transparent, translucent or tooth colored coating on teeth to which it is applied and releasing said at least one antimicrobial agent over a sustained period of time into contact with infected sites on said teeth.

2. The composition of claim 1 wherein the liquid vehicle is ethanol.

3. The composition of claim 1 wherein the weight ratio of benzoin to dentally acceptable antimicrobial agent is in the approximate range 10:1 to 1:10.

4. The composition of claim 1 including a plurality of dentally acceptable antimicrobial agents.

5. The composition of claim 1 wherein the antimicrobial agent is chlorhexidine acetate.

* * * * *